United States Patent
Sharma et al.

(10) Patent No.: US 8,961,940 B2
(45) Date of Patent: *Feb. 24, 2015

(54) MOUTH RINSES AND TOOTH SENSITIVITY TREATMENT COMPOSITIONS

(71) Applicant: Johnson & Johnson Consumer Companies, Inc., Skillman, NJ (US)

(72) Inventors: Deepak Sharma, Flemington, NJ (US); Roger Mifsud, Bridgewater, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/288,939

(22) Filed: May 28, 2014

(65) Prior Publication Data

US 2014/0271502 A1    Sep. 18, 2014

Related U.S. Application Data

(62) Division of application No. 13/608,814, filed on Sep. 10, 2012, now Pat. No. 8,771,651.

(51) Int. Cl.
| | | |
|---|---|---|
| *A61K 8/34* | (2006.01) |
| *A61K 8/362* | (2006.01) |
| *A61K 8/46* | (2006.01) |
| *A61Q 11/00* | (2006.01) |
| *A61K 8/365* | (2006.01) |
| *A61K 8/97* | (2006.01) |

(52) U.S. Cl.
CPC . *A61K 8/34* (2013.01); *A61K 8/463* (2013.01); *A61Q 11/00* (2013.01); *A61K 8/362* (2013.01); *A61K 8/365* (2013.01); *A61K 8/97* (2013.01); *A61K 8/347* (2013.01)
USPC ................................ 424/49; 424/56; 424/401

(58) Field of Classification Search
USPC .................................. 514/781; 512/20, 22, 26
See application file for complete search history.

(56) References Cited

U.S. PATENT DOCUMENTS

| | | | | |
|---|---|---|---|---|
| 5,824,289 A | * | 10/1998 | Stoltz | ............................... 424/45 |
| 5,939,048 A | | 8/1999 | Alfano et al. | |
| 6,042,812 A | | 3/2000 | Sanker et al. | |
| 7,153,493 B2 | | 12/2006 | Nelson et al. | |
| 7,435,409 B2 | | 10/2008 | Nelson et al. | |
| 2006/0280852 A1 | | 12/2006 | Harvey et al. | |
| 2011/0027197 A1 | * | 2/2011 | Sharma | ........................... 424/55 |

FOREIGN PATENT DOCUMENTS

| | | |
|---|---|---|
| EP | 0242977 | 11/1991 |
| EP | 2281548 A2 | 2/2011 |
| WO | WO 2010/126753 A2 | 11/2010 |

* cited by examiner

*Primary Examiner* — Walter Webb

(57) ABSTRACT

The present invention relates to tooth sensitivity treatment compositions, including mouth rinses, comprising $C_2$-$C_5$ diacid, triacid or tetraacid salts and a tastemasking agent(s). Methods for using the compositions are also disclosed.

20 Claims, No Drawings

MOUTH RINSES AND TOOTH SENSITIVITY TREATMENT COMPOSITIONS

CROSS-REFERENCE TO RELATED APPLICATION

This application is a divisional of U.S. application Ser. No. 13/608,814 (pending) which was filed on Sep. 10, 2012, the entirety of which is hereby incorporated by reference as if fully set forth herein.

FIELD OF THE INVENTION

The present invention relates to tooth sensitivity treatment compositions, including mouth rinses, comprising $C_2$-$C_5$ diacid, triacid or tetraacid salts and a taste masking agent(s). Methods for using the compositions are also disclosed.

BACKGROUND OF THE INVENTION

Many people suffer from sensitive teeth, and this condition is often referred as dentinal hypersensitivity. It is defined as, and used herein to mean, a transient pain arising from exposed dentin, typically in response to chemical, thermal, tactile or osmotic stimuli that cannot be explained by any other dental defect or pathology. Erosion of the outer surface of the tooth and/or gum recession often results in exposure of dentinal tubules. Any stimuli (high levels of sugar, heat, or cold) that causes a rapid movement of the biological fluid in the exposed dentinal tubules then results in distortion of intradental nerves and generates a pain response. The mechanisms of pain transmission across dentin are not fully understood but both nerve desensitizers and dentin tubule occluding agents have been used to treat teeth sensitivity. Special toothpastes, which contain potassium nitrate and/or bioglass, amorphous calcium phosphate etc., are regularly used by consumers suffering from dentinal sensitivity. Another agent that is used to treat tooth sensitivity is potassium oxalate. Although potassium oxalate is effective in mitigating dentinal sensitivity, there are several problems with it.

Compositions containing salts of $C_2$-$C_5$ diacids such as potassium oxalate tend to have a bad flavor and are difficult to taste mask. Flavor notes such as citrus, including berry, and herbal notes such as green tea fail to achieve high levels of taste masking for better consumer acceptability. Moreover, even mint flavors fall short of such high levels of consumer acceptable taste masking. There is, therefore, a continuing need for tooth sensitivity treatment compositions containing $C_2$-$C_5$ diacid, triacid or tetraacid salts, which have improved flavor acceptability.

SUMMARY OF THE INVENTION

It has been discovered that the aforementioned objective can be achieved by the compositions provided herein. In one embodiment, the present invention provides a composition for treating sensitive teeth comprising from about 0.1% to about 3% of at least one $C_2$-$C_5$ diacid, triacid or tetraacid salt; an effective taste masking amount of at least one vanilla flavor extract; from about 0.001% to about 0.25% of menthol and/or a derivative thereof and at least one orally acceptable solvent.

DETAILED DESCRIPTION OF THE INVENTION

The compositions of the present invention can comprise, consist of, or consist essentially of the essential elements and limitations of the invention described herein, as well any of the additional or optional ingredients, components, or limitations described herein. The term "comprising" (and its grammatical variations) as used herein is used in the inclusive sense of "having" or "including" and not in the exclusive sense of "consisting only of."

The terms "a" and "the" as used herein are understood to encompass the plural as well as the singular.

Unless otherwise indicated, all documents cited are, in relevant part, incorporated herein by reference; the citation of any document is not to be construed as an admission that it is prior art with response to the present invention. Furthermore, all documents incorporated herein by reference in their entirety are only incorporated herein to the extent that they are not inconsistent with this specification.

The phrase "effective taste masking amount" means the concentration or quantity or level of the vanilla flavor extract of the present invention that can attain a particular aesthetic or taste masking end with respect to the adverse taste of $C_2$-$C_5$ diacid, triacid or tetraacid salt(s).

The phrase "orally acceptable" means that the carrier is suitable for application to the surfaces of the oral cavity or ingestion by a living organism including, but not limited to, mammals and humans without undue toxicity, incompatibility, instability, allergic response, and the like.

By "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouth rinse, solutions, mousse, foam, denture care product, mouth spray, lozenge or chewable tablet. The oral care composition may also be incorporated onto floss, strips or films for direct application or attachment to oral surfaces or integrated into a device or applicator such as a toothbrush or roll-ons. Such applicators may be for single or multiple use.

All percentages, parts and ratios are based upon the total weight of the composition of the present invention, unless otherwise specified. All such weights as they pertain to the listed ingredients are based on the level of the particular ingredient described and, therefore, do not include carriers or by-products that may be included in commercially available materials, unless otherwise specified.

The phrase "reduced level" or "essentially free" of alcohol means an amount of a C2-C4 monohydric alcohol up to 10% v/v (or about 10% v/v), optionally, up to 5% v/v (or about 5% v/v), optionally, up to 1.0% v/v (or about 1.0% v/v), optionally up to 0.1% v/v (or about 0.1% v/v) by volume of the total composition. Optionally, the compositions of the present invention are free of C2-C4 monohydric alcohols.

The compositions of the present invention may be in the form of mouth washes, mouth rinses, dentifrices, toothpastes, gels, solutions or strips such as non-peroxide tooth whitening strips and the like.

The $C_2$-$C_5$ Diacid, Triacid, or Tetraacid Salt

The compositions of the present invention comprise at least one $C_2$-$C_5$ diacid, triacid, or tetraacid salt. Suitable $C_2$-$C_5$ diacid, triacid, or tetraacid salts include sodium or potassium salts of include, but are not limited to, oxalic, citric, and propane-1,2,3-tricarboxylic acid salts.

Examples of suitable diacids salts include, but are not limited to, alkali metal salts of oxalic acid, succinic acid, methylsuccinic acid, diglycolic acid, glutaric (i.e. pentanedioic)acid, 3,5,5-trimethylpentanedioic acid, hexanedioic acid, 3, 5,5-trimethylhexanedioic acid, 2,4,4-trimethylhexanedioic acid, decanedioic acid, undecanedioic acid, dodecanedioic acid, 1,4-cyclohexanedicarboxylic acid, cyclohexane-1,4-diacetic acid, maleic acid, citraconic acid, itaconic acid, fumaric acid, oxalic acid, terephthalic acid, phthalic acid, and isophthalic acid, hydroxysuccinic acid, malonic acid, adipic acid, sebacic acid, and tartaric acid, optionally, oxalic acid, succinic acid, or optionally, oxalic acid.

Examples of suitable triacids salts include, but are not limited to, alkali metal salts of citric acid.

Examples of suitable tetraacids salts include, but are not limited to, alkali metal salts of 1,1,2,2-ethanetetracarboxylic acid; 1,1,2,3-propanetetracarboxylic acid; 1,1,4,4-butanetetracarboxylic acid; 1,2,4, 5-benzenetricarboxylic acid and ethylenediaminetetraacetic acid, or optionally, 1,1,2,2-ethanetetracarboxylic acid.

In certain embodiments, the C2-C5 diacid, triacid, or tetraacid is a sodium or potassium salt of oxalic, citric, and propane-1,2,3-tricarboxylic or mixtures thereof, optionally, potassium oxalate, potassium citrate and mixtures thereof. In certain embodiments the $C_2$-$C_5$ diacid, triacid, or tetraacid salt is potassium oxalate. Suppliers of potassium oxalate include Dr. Paul Lohmann GmbH KG (Emmerthal, Germany) and Canton Lab. Pvt. Ltd (Makapura, Vadodara, India).

In certain embodiments, the $C_2$-$C_5$ diacid, triacid, or tetraacid salt is present at concentrations of from about 0.1% to about 3%, optionally from about 1% to about 2%, optionally from about 1.2% to about 1.6%, or, optionally about 1.4%, by weight of the total composition.

Vanilla Flavor Extract

The compositions of the present invention further comprise at least one vanilla flavor component. Illustrative, but nonlimiting, examples of suitable vanilla flavor components include vanillin, ethyl vanillin, heliotropine, propenyl guaethol, vanilla extracts, veratraldehyde, 4-cis-heptenal, diacetyl, butyl lactate, ethyl lactate, methyl-para-tert-butyl phenyl acetate, gamma and delta hexalactone and heptalactone, benzodihydropyrone, butter starter distillate, delta tetradecalactone, butyraldehyde, and mixtures thereof. In certain embodiments, the vanilla flavor component is selected from vanillin, ethyl vanillin, heliotropine, 4-cis-heptenal, diacetyl, and methyl-para-tert-butyl phenyl acetate or mixtures thereof. In certain other embodiments the vanilla is selected from the group consisting of vanillin, ethyl vanillin or mixtures thereof. Suppliers of ethyl vanillin or vanillin include Symrise (Goose Creek, S.C.), Firmenich, IFF, Givaudan, AM Todd, Virginia Dare, etc. Suitable solvents or diluents include, but are not limited to, propylene glycol, neobee (medium chain triglycerides supplied by Stepan Lipid Nutrition), and others commonly used in the flavor industry and mixtures thereof. A more detailed discussion of vanilla flavor extracts can be found in US Patent Publication US 2006/0280852 to Harvey et al., herein incorporated by reference in its entirety.

In certain embodiments, the vanilla flavor component is present at an effective taste masking amount. In other embodiments, the vanilla flavor extract is present at concentrations of from about 0.001% to about 0.12%, optionally from about 0.006% to about 0.03%, or optionally from about 0.012% to about 0.015%.

Menthol and/or Menthol Derivative

The compositions of the present invention further comprise menthol ($CH_3C_6H_9(C_3H_7)OH$), also known as hexahydrothymol. Menthol, in addition to any antiseptic properties, provides a cooling, tingling sensation. Also useful herein are menthol derivatives. Suitable menthol derivatives include, but are not limited to, (+)-neo-menthol; menthone; (+)-isomenthone; menthyl acetate; menthyl isovalerate; (−)-menthyl lactate; para-menth-1-en-3ol; piperitone; (−)-menthol ethylene glycol carbonate; (−)-menthol 1-and 2-propylene glycol carbonate; (−)-menthone 1,2-glycerol ketal; (+)-menthone 1,2-glycerol ketal; mono-menthyl succinate and mixtures thereof. The menthol and/or menthol derivatives can be provided in the form of mint oils including, but not limited to one or more of the following: mentha piperita mint oil; mentha arvensis mint oil; mentha spicata mint oil; mentha cardiaca mint oil; rose mitcham mint oil; corn mint oil; Japanese peppermint oil; Chinese peppermint oil; and combinations thereof. Suppliers of the menthol or menthol derivative include Jindal Drugs Limited (Navi Mumbai, India) and Symrise (Goose Creek, S.C.).

In certain embodiments, menthol or menthol derivative is present at concentrations of at least about 0.001%, optionally from about 0.001% (or greater than about 0.001%) to about 0.25%, optionally from about 0.01% to about 0.15%, optionally from about 0.05% to about 0.1%, or, optionally about 0.07%, by weight of the total composition.

In addition to the menthol or menthol derivative, or alternatively, the composition of the present invention may comprise a sensate agent selected from the group consisting of a carboxamide derivative, cyclohexanecarboxamide, dimethyl menthyl succinimide, menthyl lactate (available under the trade name Frescolat ML from Symrise GmbH & Co., Holzminden, Germany), menthone glycerin acetal (available under the trade name Frescolat MGA from Symrise GmbH & Co., Holzminden, Germany), menthoxypropanediol (commercially available under the trade name Coolact 10 and Coolact P (−)-isopulegol from Takasago Int'l Corp., Tokyo, Japan); neoisomenthol, neomenthol, isomenthol, PMD 38 p-menthane-3,8,-diol, (2R)-3-(1-menthoxy)propane-1,2-diol, (2RS)-3-(1-menthoxy)propane-1,2-diol; N-ethylpmenthane-3-carboxamide (WS-3), ethyleneglycol p-menthane-3-carboxylate (WS-4), ethyl 3-(p-menthane-3-carboxamido)acetate (WS-5), N-(4-methoxyphenyl)-p-menthane-3-carboxamide (WS-12), N-t-butyl-p-menthane-carboxamide (WS-14),2-isopropyl-N-2,3-trimethylbutyramide (WS-23), 1-glyceryl p-menthane-3-carboxylate (WS-30) (all commercially available from Millennium Chemicals, Hunt Valley, Md., USA); non-menthol derivatives such as phenol derivatives, e.g., thymol and eugenol, Icilin (Phoenix Pharmaceuticals, Belmont, Calif., USA), 2(5H)-NIPF (Nestec, Vevey, Switzerland), 4-methyl-3-(1-pyrrolidinyl)2[5H]-furanone, MPD vanillyl acetal (Takasago Int'l Corp., Tokyo, Japan) Hotact VBE (Lipo Chemicals, Inc., Paterson, N.J., USA), or capsaicin (derivative of cayenne pepper).

In certain embodiments, the sensate agent can be present, with or without the menthol and/or menthol derivative, at concentrations of from about 0.001% to about 1.0%, optionally from about 0.01% to about 0.5%, or optionally from about 0.1% to about 0.4% by weight of the total composition.

Optional Components

The compositions of the present invention may further comprise optional components (collectively referred to as orally acceptable carriers or excipients) which are described in the following paragraphs along with non-limiting examples. These orally acceptable carrier materials include one or more compatible solid or liquid excipients or diluents which are suitable for topical oral administration. By "compatible" is meant that the components of the composition are capable of being commingled without interaction in a manner which would substantially reduce composition stability and/or efficacy. Suitable carriers or excipients are well known in the art. Their selection will depend on secondary considerations like taste, cost, and shelf stability, etc. Although a general list of optional components is provided below, a more detailed discussion of suitable optional components (including excipients and carriers) can be found in US Patent Publication 20110089073 to Baig et al., herein incorporated by reference in its entirety.

Alkyl Sulfate Surfactant

Oral liquid compositions also contain at least one alkyl sulfate surfactant. In certain embodiments, suitable alkyl sulfate surfactants include, but are not limited to sulfated $C_8$ to $C_{18}$, optionally sulfated $C_{10}$ to $C_{16}$ even numbered carbon chain length alcohols neutralized with a suitable basic salt such as sodium carbonate or sodium hydroxide and mixtures thereof such that the alkyl sulfate surfactant has an even numbered $C_8$ to $C_{18}$, optionally $C_{10}$ to $C_{16}$, chain length. In certain embodiments, the alkyl sulfate is selected from the group consisting of sodium lauryl sulfate, hexadecyl sulfate and mixtures thereof. In certain embodiments, commercially available mixtures of alkyl sulfates are used. A typical percentage breakdown of alkyl sulfates by alkyl chain length in commercially available sodium lauryl sulfate (SLS) is as follows:

| Alkyl Chain Length | Component Percentage in SLS |
| --- | --- |
| $C_{12}$ | >60% |
| $C_{14}$ | 20%-35% |
| $C_{16}$ | <10% |
| $C_{10}$ | <1% |
| $C_{18}$ | <1% |

Suitable commercially available mixtures include Stephanol WA-100 NF USP (Stepan, Northfield, Ill.), Texappon K12 G PH (Cognis, Carlstadt, N.J.) and mixtures thereof.

In certain embodiments, the amount of the alkyl sulfate surfactant added to the composition can be from 0.01% (or about 0.01%) to 2.0% (or about 2.0%) w/v, optionally from 0.03% (or about 0.03%) to 0.5% (or about 0.5%) w/v, or optionally from 0.04% (or about 0.04%) to 0.35% (or about 0.35%) w/v of the composition.

In certain embodiments, the ratio of the solvent system to the alkylsulfate surfactant in the composition should be from 360:1 (or about 360:1) to 10:1 (or about 10:1), optionally from 100:1 (or about 100:1) to 20:1 (or about 20:1).

Additional Surfactant

In certain embodiments, the present invention contains a surfactant in addition to the alkyl sulfate surfactant to aid in solubilization of essential oils if present, provided such additional surfactants do not affect the bioavailability of the essential oils. Suitable examples include additional anionic surfactants, nonionic surfactants, amphoteric surfactants and mixtures thereof.

Anionic surfactants useful herein include, but are not limited to, sarcosine type surfactants or sarcosinates; taurates such as sodium methyl cocoyl taurate; sodium lauryl sulfoacetate; sodium lauroyl isethionate; sodium laureth carboxylate; sodium dodecyl benzenesulfonate and mixtures thereof. Many suitable anionic surfactants are disclosed in U.S. Pat. No. 3,959,458, to Agricola, et al., herein incorporated by reference in its entirety.

Nonionic surfactants which can be used in the compositions of the present invention include, but are not limited to, compounds produced by the condensation of alkylene oxide groups (hydrophilic in nature) with an organic hydrophobic compound which may be aliphatic or alkyl-aromatic in nature. Examples of suitable nonionic surfactants include, but are not limited to, alkyl polyglucosides; ethoxylated hydrogenated castor oils available commercially for example under the trade name CRODURET (Croda Inc., Edison, N.J.), and/or; fatty alcohol ethoxylates; polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; and mixtures thereof.

The amphoteric surfactants useful in the present invention include, but are not limited to, derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Examples of suitable amphoteric surfactants include, but are not limited alkylimino-diproprionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolines, alkyl betaines, alkylamido betaines, alkylamidopropyl betaines, alkyl sultaines, alkylamido sultaines, and mixtures thereof. In certain embodiments, the amphoteric surfactant is selected from the group consisting of alkylamidopropyl betaines, amphoacetates such as sodium lauroamphoacetate and mixtures thereof. Mixtures of any of the above mentioned surfactants can also be employed. A more detailed discussion of anionic, nonionic and amphoteric surfactants can be found in U.S. Pat. No. 7,087,650 to Lennon; U.S. Pat. No. 7,084,104 to Martin et al.; U.S. Pat. No. 5,190,747 to Sekiguchi et al.; and U.S. Pat. No. 4,051,234, Gieske, et al., each of which patents are herein incorporated by reference in their entirety.

In certain embodiments, the additional surfactant is a taurate. In one embodiment, the additional surfactant is sodium methyl cocoyl taurate.

When an alkyl sulfate surfactant and essential oils are present, the additional surfactant can be added at a concentration of from about 0.01% (or about 0.01%) to 2.0% (or about 2.0%) w/w, optionally from 0.01% (or about 0.01%) to 0.5% (or about 0.5%) w/w, or optionally from 0.01% (or about 0.01%) to 0.2% (or about 0.2%) w/w.

Essential Oils

In certain embodiments, the compositions of the present invention may contain at least one essential oil in addition to what may be provided by the oils previously described as sources for the menthol and/or menthol derivatives.

Thymol, [$(CH_3)_2CHC_6H_3(CH_3)OH$, also known as isopropyl-m-cresol], is only slightly soluble in water but is soluble in alcohol, and its presence is one of the reasons alcohol was necessary in the well-established, high alcohol commercial mouth rinses. Methyl salicylate, [$C_6H_4OHCOOCH_3$, also known as wintergreen oil], additionally provides flavoring. Eucalyptol ($C_{10}H_{18}O$, also known as cineol) is a terpene ether and provides a cooling, spicy taste.

In certain embodiments, the total amount of essential oils present in the disclosed compositions can be from 0.001% (or about 0.001%) to 0.35% (or about 0.35%) w/v, or optionally from 0.16% (or about 0.16%) to 0.28% (or about 0.28%) w/v of the composition.

In some embodiments, the compositions of the present invention contain thymol and additionally eucalyptol, or methyl salicylate, or mixtures thereof. Optionally, the composition contains all three of these essential oils.

In certain embodiments, thymol is employed in amounts of from 0.001% (or about 0.001%) to 0.25% (or about 0.25%) w/v, or optionally from 0.04% (or about 0.04%) to 0.08% (or about 0.08%) w/v of the composition. In certain embodiments, eucalyptol may be employed in amounts of from 0.001% (or about 0.001%) to 0.25% (or about 0.25%) w/v, or optionally from 0.01% (or about 0.01%) to 0.11% (or about 0.11%) w/v of the composition, but, in other embodiments, no more than 0.05% (or about 0.05%), or optionally 0.03% (or about 0.03%) w/v of the composition. In certain embodiments, methyl salicylate may be employed in amounts of from 0.001% (or about 0.001%) to 0.25% (or about 0.25%) w/v, or optionally from 0.04% (or about 0.04%) to 0.08% (or about 0.08%) w/v of the composition.

In certain embodiments, the compositions of the invention include an orally acceptable solvent. Orally acceptable solvents include, but are not limited to, water, $C_2$-$C_4$ monohydric alcohols, propylene glycol, and mixtures thereof. When present, the $C_2$-$C_4$ monohydric alcohols are at a reduced level.

The compositions of the present invention may also include one or more optional ingredients nonexclusively including a thickening agent, humectants, chelating agents, whitening agents, and additives such as flavorants, preservatives, pH adjusting agents, and the like. The pH of the compositions of this invention is optionally maintained in the range of from about 5 to about 7.5, or optionally from about 5.5 to about 7.

Commercially available thickening agents, which are capable of imparting the appropriate viscosity to the compositions, are suitable for use in this invention. Examples of suitable thickening agents nonexclusively include: mono or diesters of 1) polyethylene glycol of formula: HO—$(CH_2CH_2O)_z$H, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, or optionally PEG-150 distearate which is available from the Stepan Company of Northfield, Ill. or from Comiel, S.p.A. of Bologna, Italy under the trade name, "PEG 6000 DS".

Commercially available humectants are suitable for use in the present invention. The humectant may be present in an amount of from about 0% to about 20%, optionally from about 0.5% to about 15%, or optionally from about 0.5% to about 10%, based on the overall weight of the composition. Examples of suitable humectants nonexclusively include: 1) water soluble liquid polyols selected from the group comprising or consisting or sorbital, glycerine, propylene glycol, hexylene glycol, butylene glycol, dipropylene glycol, and mixtures thereof; 2) polyalkylene glycol of the formula: HO—$(R"O)_b$—H, wherein R" is an alkylene group having from about 2 to about 3 carbon atoms and b is an integer of from about 2 to about 10; 3) polyethylene glycol ether of methyl glucose of formula $CH_3$—$C_6H_{10}O_5$—$(OCH_2CH_2)_c$—OH, wherein c is an integer from about 5 to about 25; 4) urea; and 5) mixtures thereof, In certain embodiments, the humectant is a mixture sorbitol and propylene glycol.

Examples of suitable chelating agents include those which are capable of protecting and preserving the compositions of this invention. Optionally, the chelating agent is ethylenediamine tetracetic acid ("EDTA"), or optionally is tetrasodium EDTA, available commercially from Dow Chemical Company of Midland, Mich. under the trade name, "Versene 100XL" and is present in an amount, based upon the total weight of the composition, from about 0 to about 0.5%, or optionally from about 0.05% to about 0.25%.

Suitable preservatives include, sodium benzoate, and polysorabate and are present in the composition in an amount, based upon the total weight of the composition, from about 0 to about 0.2%, or optionally from about 0.05% to about 0.10%.

The above described compositions may be prepared by combining the desired components in a suitable container and mixing them under ambient conditions in any conventional mixing means well known in the art, such as a mechanically stirred propeller, paddle, and the like. The order of mixing is not critical.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

In certain embodiments, the compositions of the present invention are free of or essentially free of chewing gum or chewing gum base. Chewing gum or chewing gum bases tend to trap or other inhibit availability of oral care agents such as the $C_2$-$C_5$ diacid, triacid or tetraacid salts of the present invention so that they are unable to perform their intended function. Moreover, the melting and mixing of highly viscous gum mass (i.e., of the chewing gum or chewing gum base) makes controlling the dosing accuracy and uniformity of such oral care agents difficult. "Essentially free" as used with respect to chewing gum or chewing gum base is defined as formulations having less than 5% (or about 5%), optionally, 3% (or about 3%), optionally, 1% (or about 1%), or optionally 0.1, or optionally, 0.01% (or about 0.01%), by weight (w/v) of the total composition of a bioavailability affecting compound. In certain embodiments, the bioavailability affecting compound can include, but is not limited to, polyethylene oxide/polypropylene oxide block copolymers such as poloxamers; cyclodextrins; polysorbates such as Tweens; and mixtures thereof. Chewing gums and chewing gum base are described in more detail in, previously incorporated by reference, Patent Publication US 2006/0280852 to Harvey et al.

EXAMPLES

The following examples are illustrative only and should not be construed as limiting the invention in any way. Those skilled in the art will appreciate that variations are possible which are within the spirit and scope of the appended claims.

Flavor Acceptability Rating

Compositions of the present invention containing potassium oxalate were evaluated for flavor acceptability. Evaluation of the flavor of the compositions was conducted by test group of 190 members. The members were asked to swish 10 ml of each of compositions of Examples A through E (Table 1) in their mouths for 60 seconds, expectorate and provide a flavor acceptability rating on a scale of 1 to 9, using the following flavor overall liking scale: 0-4=unacceptable; 5=neutral; and 6-9=acceptable. The compositions of Table 1 were prepared using conventional mixing technology.

TABLE 1

| Ingredient | Example A (Comparative Example) Conc. (%) | Example B (Comparative Example) Conc. (%) | Example C (Comparative Example) Conc. (%) | Example D (Comparative Example) Conc. (%) | Example E (Comparative Example) Conc. (%) | Example F (Inventive Example) Conc. (%) |
| --- | --- | --- | --- | --- | --- | --- |
| Purified water, | 66.6781 | 66.6000 | 60.73000 | 66.6500 | 60.7600 | 60.6500 |
| 190 proof ethyl alcohol | 9.6235 | 9.6235 | — | 9.6235 | — | — |
| Sorbitol solution, 70% | 19.3311 | 19.3311 | 27.3474 | 19.3311 | 27.3474 | 27.3474 |
| Potassium oxalate monohydrate | 1.9247 | 1.9247 | 1.2762 | 1.9247 | 1.2762 | 1.2762 |
| Phosphoric acid NF | 1.2992 | 1.2992 | 0.2188 | 1.2992 | 0.2188 | 0.2188 |
| Sodium saccharin | 0.2900 | 0.2900 | 0.0456 | 0.2900 | 0.0456 | 0.0456 |
| Poloxamer 407 | 0.2406 | 0.2406 | 0.2279 | 0.2406 | 0.2279 | 0.2279 |
| Eucalyptol | 0.0887 | 0.0887 | — | 0.0887 | — | — |
| Methyl salicylate | 0.0638 | 0.0638 | — | 0.0638 | — | — |
| Thymol | 0.0615 | 0.0615 | — | 0.0615 | — | — |
| Menthol (mint flavor component) | 0.0385 | 0.0423 | — | 0.0423 | — | — |
| Sucralose powder NF | 0.0385 | 0.0385 | 0.0182 | 0.0385 | 0.0182 | 0.0182 |
| Sodium fluoride | 0.0213 | 0.0213 | — | 0.0213 | — | — |
| Color | 0.0005 | 0.0005 | — | 0.0005 | — | — |
| Benzoic acid | — | — | 0.1367 | — | 0.1367 | 0.1367 |
| PEG 400 | — | — | 7.2926 | — | 7.2926 | 7.2926 |
| Glycerin | — | — | 2.2789 | — | 2.2789 | 2.2789 |
| Cocamidopropyl betaine | — | — | 0.0912 | — | 0.0912 | 0.0912 |
| Sodium lauryl sulfate NF | — | — | 0.0912 | — | 0.0912 | 0.0912 |
| Flavor - Citrus family | — | 0.3750 | — | — | — | — |
| Flavor - Herbal (berry) | — | — | 0.3250 | — | — | — |
| Flavor - Herbal (Green tea) | — | — | — | 0.3250 | — | — |
| Flavor - Mint | 0.3000 | — | — | — | 0.3000 | 0.2850 |
| Ethyl vanillin | — | — | — | — | — | 0.0400 |
| TOTAL | 100.0000 | 100.0007 | 100.0797 | 100.0007 | 100.0847 | 99.9997 |
| Flavor Overall Liking Scale(1 to 9) mean rating. (p = 0.064) | 3.5 | 3.0 | 5.2 | 2.8 | 5.2 | 6.2 |

Based on the Flavor Overall Liking Scale, the results of Table 1 show that only the inventive Example F which contains the vanillin flavor extract with the oxalate salt and menthol provided a score (6.2 score) in the high 5 to greater than 6 range. Notably, formulations without the vanillin flavor extract, namely those containing either mint flavor plus essential oils (3.5 score), citrus flavor plus essential oils (3.0 score), herbal green tea plus essential oils (2.8 score) or mint flavor alone (5.2 score) all resulted in scores of low 5 or below.

Additional embodiments of the present invention are exemplified in Examples 1 and 2 of Table 2 and can be prepared using conventional mixing technology. Each of Examples 1 and 2 provide scores (5.9 score and 5.7 score, respectively) in the high 5 range.

TABLE 2

| Ingredient | Example 1 Concentration (%) | Example 2 Concentration (%) |
| --- | --- | --- |
| Purified water | 82.7343 | 82.8255 |
| 190 proof ethyl alcohol | — | — |
| Sorbitol solution, 70% | 9.6098 | 9.6098 |
| Potassium oxalate monohydrate | 1.3454 | 1.3454 |
| Phosphoric acid NF | 0.3350 | 0.3350 |
| Sodium saccharin | 0.0480 | 0.0200 |
| Poloxamer 407 | 0.2402 | 0.2402 |
| Sucralose powder NF | 0.0192 | 0.0400 |
| Sodium lauryl sulfate NF | 0.0500 | 0.0500 |
| Sodium benzoate | 0.1441 | 0.1441 |
| Sodium methyl cocoyl taurate | 0.0600 | 0.0600 |
| Propylene glycol | 5.0000 | 5.0000 |
| Ethyl vanillin | 0.0400 | 0.0400 |
| Menthol | 0.0701 | 0.0701 |
| Thymol | 0.0640 | 0.0640 |
| Methyl Salicylate | 0.0660 | 0.0660 |
| Eucalyptol | 0.0923 | 0.0300 |
| Flavor | 0.0910 | 0.0660 |
| TOTAL | 100.0000 | 100.0000 |
| Flavor Overall Liking Scale (1 to 9) mean rating. (p = 0.064) | 5.9 | 5.7 |

What is claimed is:

1. A composition for treating sensitive teeth comprising:
   i. from about 0.1% to about 3% of at least one potassium salt of a C2-C5 diacid, triacid, or tetraacid;
   ii. at least one vanilla flavor extract;
   iii. from about 0.001% to about 0.25% of menthol or a derivative thereof;
   iv. at least one orally acceptable solvent; and
   v. from about 0.01% to about 2% of an alkyl sulfate surfactant;
   wherein the composition is a toothpaste, dentifrice, tooth gel, subgingival gel, denture care product, mouth spray, lozenge or chewable tablet, and comprises up to 1% v/v of the total composition of C2-C4 monohydric alcohols.

2. The compositions according to claim 1 wherein the alkyl sulfate surfactant is an alkyl sulfate surfactant having an even numbered C8 to C18 chain length.

3. The compositions according to claim 2 wherein the alkyl sulfate surfactant is selected from the group consisting of sodium lauryl sulfate, hexadecyl sulfate and mixtures thereof.

4. The composition according to claim 1 further comprising from about 0.01% to about 2% of an additional surfactant.

5. The composition according to claim 4 wherein the additional surfactant is a taurate.

6. The composition according to claim 1 wherein the vanilla flavor extract is selected from the group consisting of vanillin, ethyl vanillin, heliotropine, propenyl guaethol, vanilla extracts, veratraldehyde, 4-cis-heptenal, diacetyl, butyl lactate, ethyl lactate, methyl-para-tert-butyl phenyl acetate, gamma and delta hexalactone and heptalactone, benzodihydropyrone, butter starter distillate, delta tetradecalactone, butyraldehyde, and mixtures thereof 7. The composition according to claim 6 wherein the vanilla flavor extract is ethyl vanillin.

8. The composition according to claim 1 wherein the composition contains from about 0.001% to about 0.12% of the vanilla flavor extract.

9. The composition according to claim 1 wherein the composition contains from about 0.01% to about 0.15% the menthol or a derivative thereof.

10. The composition according to claim 1 wherein the menthol or derivative thereof is menthol.

11. The composition of claim 1 wherein said at least one potassium salt of a C2-C5 diacid, triacid, or tetraacid is a potassium salt of oxalic acid, citric acid, propane-1,2,3,tricarboxylic acid, or a mixture thereof 12. The composition of claim 11 comprising from about 1 to about 2% of said potassium salt of oxalic acid, citric acid, propane-1,2,3,tricarboxylic acid, or a mixture thereof 13. The composition of claim 12 wherein the vanilla flavor extract is selected from the group consisting of vanillin, ethyl vanillin, heliotropine, propenyl guaethol, vanilla extracts, veratraldehyde, 4-cis-heptenal, diacetyl, butyl lactate, ethyl lactate, methyl-para-tert-butyl phenyl acetate, gamma and delta hexalactone and heptalactone, benzodihydropyrone, butter starter distillate, delta tetradecalactone, butyraldehyde, and mixtures thereof 14. The composition according to claim 13 wherein the composition contains from about 0.001% to about 0.12% of the vanilla flavor extract.

15. The composition according to claim 14 wherein the composition contains from about 0.01% to about 0.15% the menthol or a derivative thereof.

16. The composition of claim 15 wherein said at least one C2-C5 diacid, triacid, or tetraacid salt is potassium oxalate.

17. The composition according to claim 16 wherein the vanilla flavor extract is ethyl vanillin.

18. The composition according to claim 17 wherein the menthol or derivative thereof is menthol.

19. The composition according to claim 18 wherein the alkyl sulfate surfactant is sodium lauryl sulfate.

20. The composition according to claim 19 wherein the composition is free of C2-C4 monohydric alcohols.

* * * * *